United States Patent [19]
LeVeen et al.

[11] Patent Number: 5,123,909
[45] Date of Patent: Jun. 23, 1992

[54] PLAQUE CRACKER

[76] Inventors: Harry H. LeVeen, 321 Confederate Cir., Charleston, S.C. 29407; Robert F. LeVeen, 312 Lombard St., Philadelphia, Pa. 19147; Eric G. LeVeen, 19 Palmetto Rd., Charleston, S.C. 29407

[21] Appl. No.: 525,685

[22] Filed: May 21, 1990

[51] Int. Cl.$^5$ ............................................. A61B 17/00
[52] U.S. Cl. ............................................. 606/201
[58] Field of Search ............ 606/188, 151, 201; 81/129, 150, 487; 30/120.2, 120.5

[56] References Cited

U.S. PATENT DOCUMENTS

| | | | |
|---|---|---|---|
| 1,542,307 | 6/1925 | Kennedy | 81/150 |
| 3,841,212 | 10/1974 | Powell | 30/120.2 X |
| 4,079,740 | 3/1978 | Phalon | 606/188 |
| 4,087,910 | 5/1978 | Doyel | 30/120.5 |
| 4,520,719 | 6/1985 | Price | 30/120.2 X |

*Primary Examiner*—Michael H. Thaler
*Attorney, Agent, or Firm*—John S. Hale

[57] ABSTRACT

A device for cracking plaque from a blood vessel comprising a fixed jaw member assembly, a moveable jaw member and hammer assembly slidably mounted on the fixed jaw member assembly and a spring transmitting a driving force to the hammer assembly. A handle is connected to the fixed jaw member assembly and a trigger activation assembly is mounted in the handle to activate a trigger releasing the hammer assembly to transmit a driving force against the moveable jaw member and an adjacent blood vessel.

8 Claims, 3 Drawing Sheets

PLAQUE CRACKER

BACKGROUND OF THE INVENTION

In the art of vascular surgery, it is frequently desired to remove the inner layer from the vessel, which is fatty in nature, without cutting the vessel entirely through, but nevertheless cutting the inner layer to such a degree that, at a point some distance away, the blood vessel can be opened and the inner fatty sleeve pulled out of the vessel.

In an effort to solve this problem, there have been experiments in the design of an instrument which uses a guillotine type arrangement with an upper anvil member containing a dull blade resting on one side of the blood vessel and a hammerlike opposing jaw which held the blood vessel between the two members.

Experimental work has disclosed that an impact of sufficient magnitude with a dull blade to the outside of an unopened artery will fracture the intima without injury to the other layers of the artery (Arch. Surg. 1973, 107:664–668). Based upon this experimentation, a spring loaded instrument was made which activates two dull blades to deliver an impact of 4,000 gram centimeters to the outside of an artery. The dull blades were compressed against the vessel by a weak spring and impact to the dull blades was delivered by a separate, stronger spring which activates a hammer which struck a blow against the blades. This spring loaded instrument is clearly shown and described in U.S. Pat. No. 4,058,126. Although this instrument produced a linear fracture of the intima of the aorta, it was not applicable to all arteries as small arteries require a lesser impact than larger arteries. Thus, when the instrument of the '126 patent was used, a serious complication occurred in some small vessels as the blow inadvertently severed the small artery. This serious complication limited the usefulness of the instrument for vessels other than the aorta. It was thus necessary to design a new instrument which eliminates defects of past instruments and such an instrument is the subject of the present invention.

SUMMARY OF THE INVENTION

The present invention is directed towards a pistol grip plaque cracker which utilizes adjustable jaw members for adaptability in use for different size arteries and provides a hammer with selected varying striking force.

It is an object of the present invention to eliminate the defects of past instruments by providing an adjustable space between the blades or jaws which prevents contact of the two blades during impact. Such a spacing has eliminated accidental transsection of small vessels even when the impact is greater than necessary, thus satisfying a major safety requirement.

Another object of the invention is to design an instrument allowing use by one hand, which overcomes defects of previous instruments in that two hands were required to manipulate these instruments. This is important because it is sometimes imperative to have one hand free to retract, palpate or facilitate exposure of the vessel. Thus, the disadvantages of the instrument described in the '126 patent were so adverse that it had limited usefulness and little commercial value.

An important safety feature of the invention makes it impossible for the blood vessel to be inadvertently transsected by too severe an impact. This is accomplished by providing for a small spacing to be set between the blades and the impact stopped at that spaced point so that the blades do not contact one another. Thus, the external elastic coats of the vessel are thus accommodated with the small interval left between the blades. Tissue such as the adventitia and outer elastic coats of the vessel remain totally untraumatized and uninjured by the blow being transmitted to the outside of the artery. This instrument can be used on arteries as small as the carotid or popliteal arteries without the danger of transsecting the vessel.

Another object of the invention is the use of a lever which can be moved by the thumb to deflect a weak spring which engages to the moveable blade and opens and shuts the blades during the placement of vessel in the instrument. After vessel placement with the blade open, the thumb lever is released allowing the blades to gently compress the blood vessel until the plaque cracking impact is delivered. The impact is delivered by compressing a stronger spring with the hammer by squeezing the pistol grip trigger until the desired spring tension is achieved against the hammer and then releasing the hammer to transmit a plaque cracking force against the blood vessel.

In the accompanying drawings, there is shown an illustrative embodiment of the invention from which these and other of objectives, novel features and advantages will be readily apparent.

DETAILED DESCRIPTION OF THE INVENTION

Figure 1:
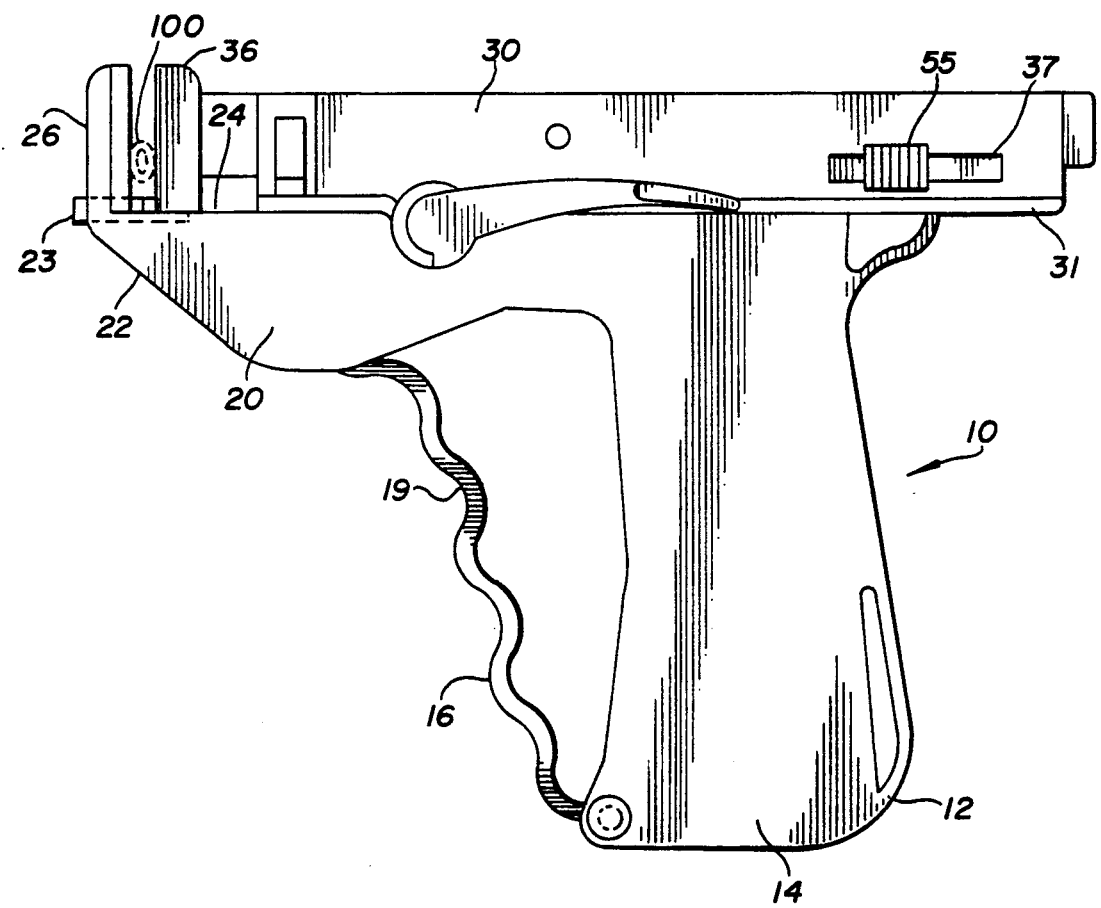
FIG. 1 is a side elevational view of the plaque cracking instrument with the jaws of the instrument engaging a blood vessel.
Figure 2:
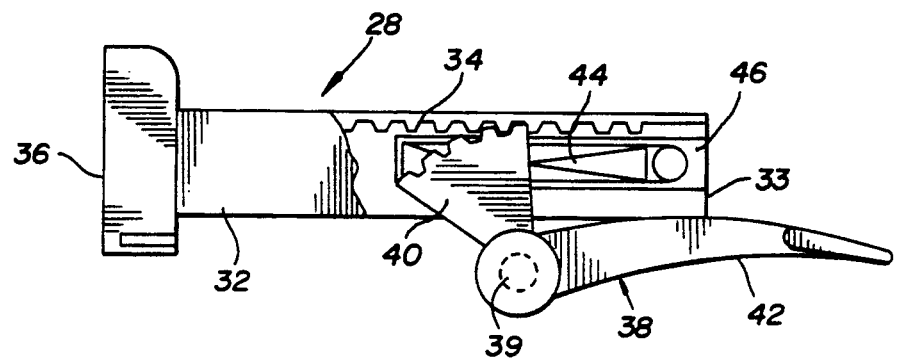
FIG. 2 is an enlarged partially broken away section of the moveable jaw assembly shown in FIG. 1.
Figure 3:
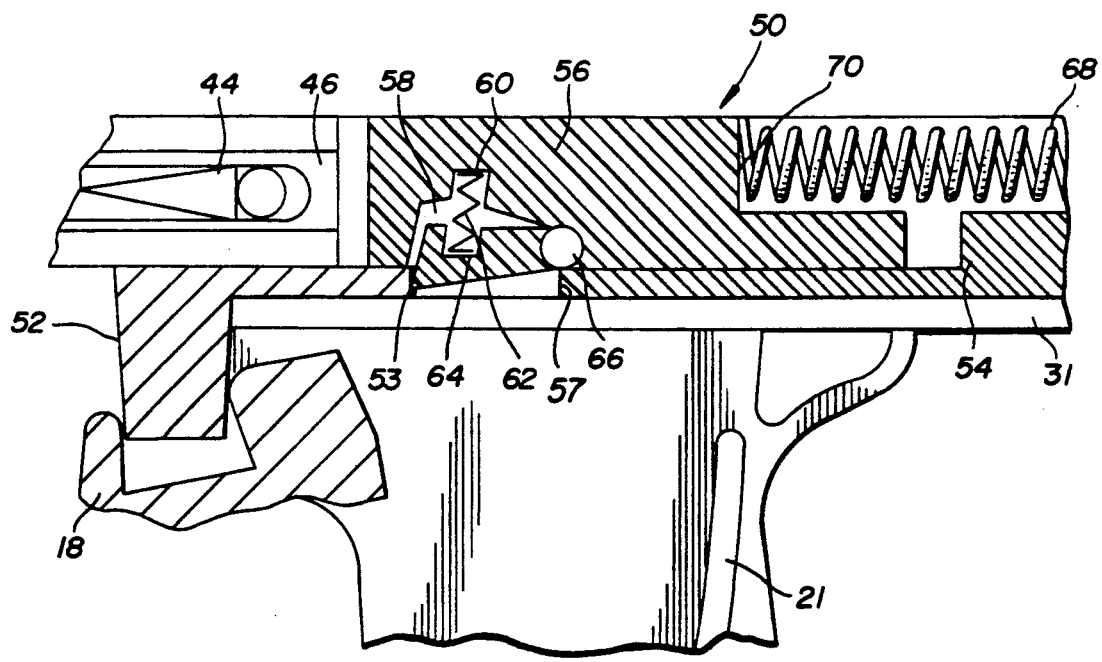
FIG. 3 is an enlarged broken away sectional view of the hammer and moveable jaw assembly of the present invention shown as the surgeon begins squeezing the handle.
Figure 4:
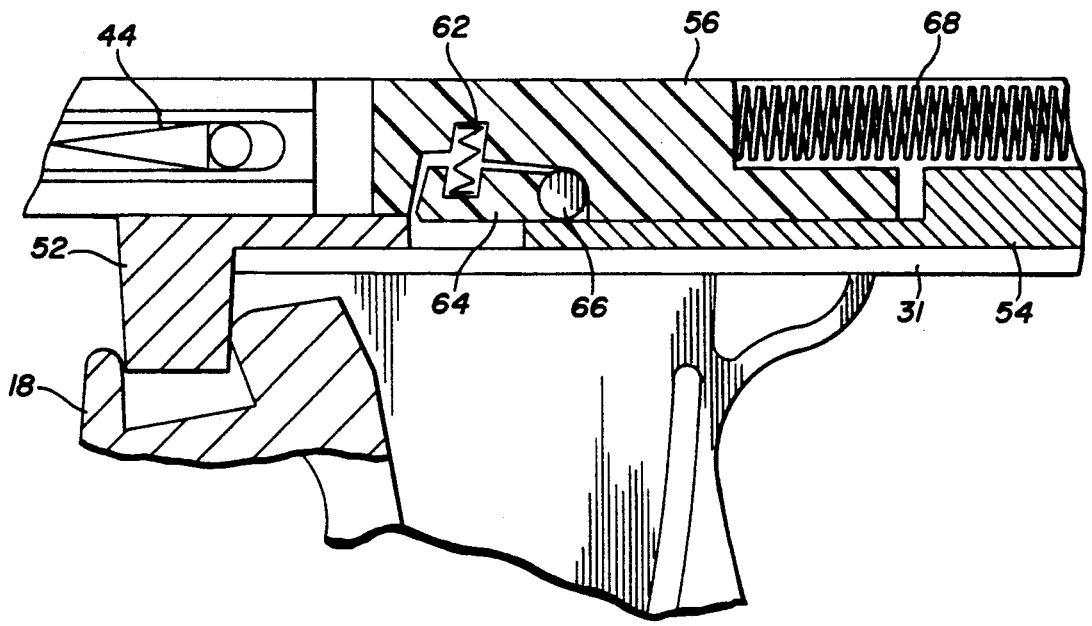
FIG. 4 is a sequential view taken from that of FIG. 3 as the hammer is cocked and the trigger has tripped the trip lever.
Figure 5:
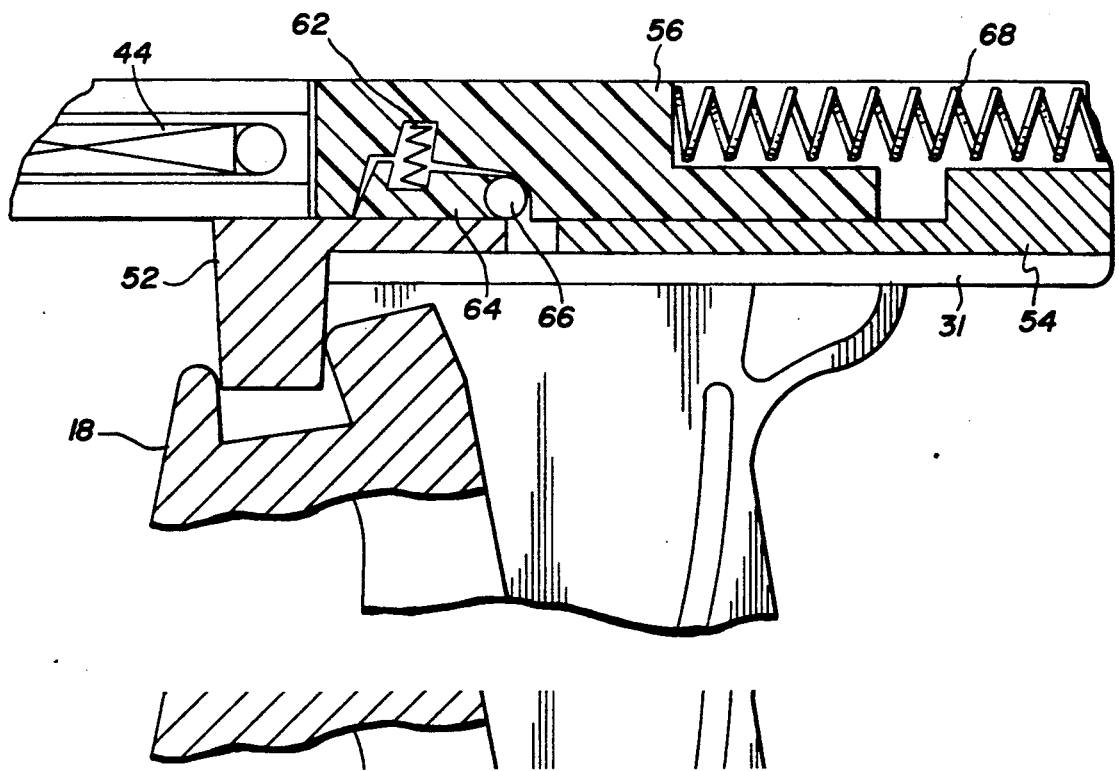
FIG. 5 is a sequential view taken from that of FIG. 4 after the hammer trips and moves forward to strike the moveable jaw assembly driving it forward to impact the vessel.

The preferred embodiment and best mode of the invention is shown in FIGS. 1–5. The plaque cracker apparatus 10 which is preferably made of plastic is constructed with a handle assembly 12, fixed jaw structure 20 and barrel housing 30 including moveable jaw assembly 28. If desired, the fixed jaw structure and handle can be integrally molded in one piece of plastic. The handle assembly 12 comprises a hollow butt 14, a trigger activator member 16 mounted inside the butt and spring biased therein as shown in FIGS. 1 and 3. The trigger activator member 16 has one end defining a trigger seat 18, as shown in FIG. 3 with an intermediate portion defining a trigger grip 19 and a distal biasing end 21. A fixed jaw structure 20 extends outward from the butt 14 as shown in FIG. 1 and is constructed with a jaw arm 22 ending in a fixed jaw 26 extending upward from the jaw arm 22. The jaw arm 22 is provided with a slot on the bottom slide surface 24 and a set screw 23. The fixed jaw structure 20 provides a housing which encloses the trigger seat 18 on the end of trigger activator member 16. A moveable jaw assembly 28 as shown in FIG. 2 is movably mounted in barrel housing 30 which in turn is secured to the top of the jaw arm 22. The moveable jaw assembly is constructed with a jaw housing 32 having an internal toothed rack 34 and ends in a moveable jaw 36. A rack drive 38 is rotatably mounted to the fixed jaw body 20 by shaft 39 and engages the rack 34 through the operation of a toothed arc drive member 40 secured to thumb lever 42; the thumb lever 42 being mounted on shaft 39. The toothed rack drive member 40 is constantly urged toward the position shown in FIG. 1 by a weak spring member 44 mounted in seat 46 formed in the rack housing 32. Thus, when an artery 100 is placed between fixed jaw 26 and the moveable jaw 36, the thumb lever 42 is released so that the spring 44 drives the rack drive member 40 along the rack 34 causing the moveable jaw 36 to engage the blood vessel 100 at a fixed distance away from the fixed jaw. It should be noted that the fixed jaw and moveable jaw 36 do not meet because they have been previously spaced by the set screw 23 on the bottom slide surface 24 of the jaw arm. This set screw serves as a stop to limit forward movement of the moveable jaw 36.

A firing assembly 50 is positioned in the barrel housing 30. The firing assembly 50 comprises a trigger member 52 which is slidably mounted on the flat base 31 of the barrel housing, an adjuster member 54 which is also slidably mounted on the base S1 of the barrel housing and a hammer 56 which is slidably mounted in the barrel housing over the upper surfaces of the adjuster member 54 and trigger 52. The adjuster member 54 is positionally adjusted in the barrel housing by adjuster knob 55 mounted in slot 37 formed in the barrel housing. The adjuster knob 55 is secured to the adjuster member 54 and extends outward through slot 37. The hammer 56 defines a trip lever seat 58 and a trip lever spring seat 60 which holds a trip lever spring 62. The trip lever spring 62 constantly urges the trip lever 64 which is housed in the trip lever seat downward against trigger 52 and out of the trip lever seat 58. The trip lever 64 is rotatably mounted on a trip axle 66 which is in turn mounted to the hammer body. A hammer spring 68 is mounted against a hammer spring seat 70 defined by the rear end of hammer 56 and the end of the barrel housing. The spring constantly urges the hammer 56 forward so that the trip lever engages camming end 53 of trigger 52. Once the trip lever 64 has been cammed upward by the trigger cam end 53 by pushing the lever against the cam surface 57 of adjuster member 54 into the trip lever seat 58, the hammer trips and is driven forward by the spring 68, striking the end 33 of the moveable jaw assembly 32 so that the moveable jaw 32 transmits force to the blood vessel 100, causing the plaque to crack and sever in the blood vessel as previously noted.

The present inventive instrument has a pistol grip so it can be manipulated with a single hand. The hammer 56 is cocked by compressing the handle trigger activator member 16 which compresses a spring to a preselected point of compression and then releases the hammer. The strength of the impact can thus be adjusted according to the size of the vessel from very strong to weak. It is thus possible to engage the artery with a blade above and below the vessel and to activate the blades with only a single hand. The other hand is therefore free to aid exposure, to retract away vital organs, to palpate the pathology and to assist in placement of the plaque cracker.

The plaque is then removed by pulling the internal severed layer out of the blood vessel, leaving the blood vessel intact. Thus, the impact of the anvil or moveable jaw 36 is controlled by the collision of the hammer 56 driven by the hammer spring 68. It is also clear that the shock or impact of this moveable jaw member 36 on the blood vessel 100 is sufficient to leave the inner layer of the blood vessel but is insufficient to cleave the outer layers of the blood vessel which surround the same.

Thus, squeezing the handle (grip 19) causes the trigger 52 to slide back. The trigger contacts the trip lever 64, pushing the trip lever and hammer 56 backwards and compressing the hammer spring 68. When the trip lever 64 contacts the end 57 of the adjuster bar 54, it is forced up and over the trigger. At this point, the hammer 56 is free to slide forward propelled by the compressed hammer spring 68. By moving the adjuster bar 54 forward or backward by slide meter or knob 55, the point at which the trip lever is released can be controlled. This in turn regulates the amount of compression on the spring 68 and the force imparted by the hammer. The hammer contacts the moveable jaw at the end of its stroke, transferring the force to the vessel.

While various embodiments of the present invention have been shown and described herein for purposes of illustration, it will be apparent that other variations and embodiments are considered to fall within the scope of the defined invention.

What is claimed is:

1. Device for cracking plaque from a blood vessel comprising a fixed jaw assembly, a moveable jaw member slideably mounted on said fixed jaw assembly, said moveable jaw member comprising a housing and a jaw secured to one end of said housing and including a toothed rack drive means comprising a toothed member and lever means engaging said toothed member, a hammer means slideably mounted on said fixed jaw assembly, means to provide said hammer means with a selective striking force against said moveable jaw assembly, handle means connected to said fixed jaw member assembly and trigger means mounted to said handle to activate said hammer means to transmit a selective striking force, said trigger means comprising a slideable trigger member and a trigger moving member mounted to said handle means.

2. A device as claimed in claim 1 wherein said means to transmit a driving force comprises a hammer assembly, said hammer assembly including spring means urging said hammer assembly toward said moveable jaw member.

3. A pistol shaped device for cracking plaque from a blood vessel comprising a handle assembly with a fixed jaw secured thereto, a barrel housing mounted on said handle assembly, a movable jaw assembly mounted in said barrel housing on said handle assembly, said moveable jaw assembly comprising a jaw, a housing secured to said jaw and drive means mounted in said barrel housing adapted to engage said moveable jaw assembly housing, said drive means comprising a slideable hammer, spring means mounted on one end of said hammer constantly urging said hammer forward towards said moveable jaw assembly housing and release means mounted to said hammer, said release means comprising a latch member rotatably secured to said hammer, said latch member being urged away from said hammer by a spring means mounted to said hammer and being adapted to release said hammer to drive said hammer forward to engage the moveable jaw assembly and transmit force to the blood vessel, hammer force adjustment means moveably mounted in said barrel housing, said adjustment means comprising a moveable member with an adjustment mechanism which extends outside of the barrel housing.

4. A device as claimed in claim 3 wherein said handle is hollow and holds a spring activated hammer member, said spring activated hammer member defining a latch seat which holds a latch member, said hammer member being slideably mounted on an adjuster bar comprising the hammer force adjustment means, which engages the latch member as the latch member is driven backward by the trigger camming it upward into the latch seat formed in the hammer member.

5. A device as claimed in claim 4 wherein said hammer force adjustment means which comprises an adjuster bar further includes a post extending from said adjuster bar through a slot formed in said barrel housing to positionally adjust the adjuster bar in said barrel housing.

6. A device as claimed in claim 3 including moveable jaw limitation means formed in said fixed jaw.

7. A device as claimed in claim 3 wherein said moveable jaw assembly comprises a housing, a jaw secured to one end of said housing, rack means secured to said housed and a toothed rack drive means engaging said rack and adapted to move said housing back and forth in said barrel housing.

8. A device as claimed in claim 18 wherein said toothed rack drive means comprises a toothed arc shaped member and lever means secured to said member.

* * * * *